(12) United States Patent
Aglen

(10) Patent No.: US 11,072,770 B2
(45) Date of Patent: Jul. 27, 2021

(54) COMPACT REACTOR FOR ENZYMATIC TREATMENT

(71) Applicant: NUAS TECNOLOGY AS, Rissa (NO)

(72) Inventor: Lars Aglen, Lysöysundet (NO)

(73) Assignee: NUAS TECNOLOGY AS, Rissa (NO)

(*) Notice: Subject to any disclaimer, the term of this patent is extended or adjusted under 35 U.S.C. 154(b) by 398 days.

(21) Appl. No.: 15/517,242

(22) PCT Filed: Oct. 5, 2015

(86) PCT No.: PCT/NO2015/050183
§ 371 (c)(1),
(2) Date: Apr. 6, 2017

(87) PCT Pub. No.: WO2016/056922
PCT Pub. Date: Apr. 14, 2016

(65) Prior Publication Data
US 2017/0306280 A1    Oct. 26, 2017

(30) Foreign Application Priority Data

Oct. 7, 2014   (NO) .................................. 20141197
Jul. 15, 2015  (NO) .................................. 20150943

(51) Int. Cl.
C12M 1/40    (2006.01)
C12M 1/12    (2006.01)
(Continued)

(52) U.S. Cl.
CPC ............ C12M 21/18 (2013.01); C12M 23/06 (2013.01); C12M 23/58 (2013.01); C12M 29/06 (2013.01);
(Continued)

(58) Field of Classification Search
CPC ...... C12M 21/18; C12M 23/06; C12M 23/58; C12M 29/06; C12M 45/09; C12M 41/22; C12M 1/04
See application file for complete search history.

(56) References Cited

U.S. PATENT DOCUMENTS 5,141,861 A    8/1992  Dale
5,733,758 A    3/1998  Nguyen
5,888,806 A    3/1999  Nguyen
7,387,769 B2*  6/2008  Erdman ................. B01J 19/245
                                                    423/432
(Continued)

FOREIGN PATENT DOCUMENTS

CN    88212729 U    11/1988
CN    201495212 U    6/2010
(Continued)

OTHER PUBLICATIONS

International Search Report and Written Opinion dated Dec. 10, 2015 (PCT/NO2015/050183).

Primary Examiner — William H. Beisner
Assistant Examiner — Danielle B Henkel
(74) Attorney, Agent, or Firm — Alix, Yale & Ristas, LLP

(57) ABSTRACT

Reactor for enzymatic hydrolysis of a raw material comprising in sequence: i)—a first heat exchanger adapted to heat the raw material supplied to the reactor to a temperature within a range that favours enzymatic hydrolysis, ii)—a reactor comprising plural in reactor chambers connected in series, separated by closable valves, iii)—a second heat exchanger adapted to heat the reaction mixture to a temperature higher than the temperature range favouring enzymatic hydrolysis, the reactor being formed with inclined tubular reactor chambers assembled to form a reactor with vertical axis, the first reactor chamber being the vertically
(Continued)

uppermost chamber of the reactor, while at least one reactor chamber is adapted to be stirred with a through-flowing inert gas.

22 Claims, 6 Drawing Sheets

(51) Int. Cl.
    *C12M 1/00*     (2006.01)
    *C12M 1/02*     (2006.01)
    *C12M 1/04*     (2006.01)

(52) U.S. Cl.
    CPC ............ *C12M 41/22* (2013.01); *C12M 45/09* (2013.01); *C12M 1/04* (2013.01)

(56) References Cited

U.S. PATENT DOCUMENTS

| | | |
|---|---|---|
| 9,232,812 B2 | 1/2016 | Soerensen et al. |
| 9,290,733 B2 | 3/2016 | Muller-Feuga |
| 2007/0298477 A1 * | 12/2007 | Kratochvil ................ C12P 7/10 435/165 |
| 2012/0288927 A1 | 11/2012 | Kaneko et al. |
| 2013/0323714 A1 | 12/2013 | Cheng et al. |
| 2015/0284754 A1 | 10/2015 | Nguyen et al. |

FOREIGN PATENT DOCUMENTS

| | | | |
|---|---|---|---|
| JP | 62278988 A | 12/1987 |
| WO | 9506111 A1 | 3/1995 |
| WO | 2006126891 A1 | 11/2006 |

* cited by examiner

COMPACT REACTOR FOR ENZYMATIC TREATMENT

BACKGROUND

The disclosure concerns a reactor for enzymatic treatment.

During enzymatic treatment of organic materials for the sake of hydrolysis (decomposition), a control of the temperature in the material and the duration of the exposure of the material for the enzymes (contact time) is a prerequisite for successful result. Too long or too short contact time will both be negative for the product of the process and can cause problems for further processing of the material and/ or be a negative for the quality of the finished product from a manufacturing process. Proper contact time is thus a central issue here.

When using industrial enzymes for hydrolysing or another form of enzymatic process, the appropriate enzymes are added to a raw material. After the enzymes have been added and distributed in the raw material, it is important that the mixture is stirred constantly to ensure good contact between enzyme and raw material. As mentioned it is also important that the enzymes are in contact with the raw material for a certain time interval. When this time interval is reached, it is thus important that the enzymatic degradation ceases quickly so that the process does not go too far. This is typically ensured by heating the mixture of raw material and enzymes to a temperature at which the enzymes are destroyed (inactivated).

A similar challenge applies to a number of other chemical processes where it is important with a homogeneous blend of the components included as well as a controlled reaction time which can neither be significantly shorter or considerably longer than the optimal one if the desired quality of the final product to be obtained.

The easiest way to achieve proper contact time is to use reactors based on "batch" principle. By batch execution a defined volume (tank or the like) is kept at certain conditions for a certain time, before the process is stopped. For enzymatic processes, as mentioned, additional heating is used to inactivate the enzyme. In an industrial production large volumes are processed, and these large volumes are difficult to heat quickly enough if run as batch. An alternative is to use a plural of small batch volumes, but this will lead to disproportionately high costs in terms of technology.

There are also other disadvantages of batch processes compared with continuous processes regardless of whether the processes involve enzymatic treatment. One such disadvantage is far more frequent starting and stopping of processes. This is labouring intensive and more difficult to automatize than continuous processes. Moreover, operating conditions during start and stop tend to vary more than what is desirable.

The goal is to have a continuous through-put of homogeneously mixed raw material which process is inactivated at a given time interval. To allow a continuous flow of raw materials to go through a large "complete mix" container is not a good solution because the contact time between the individual components will then be very difficult to control.

A reactor for the enzymatic treatment of the raw material is known from Norwegian patent no. 322 996 (WO 2006 126891). The treatment takes place in a substantially vertically arranged reactor with separate reactor chambers where the material in each chamber is mixed mechanically with a stirrer and transferred to an adjacent chamber below by utilizing gravitational forces. The reactor will ensure consistent retention time and consistent conditions for all material processed.

For the treatment especially of marine raw material, it is important that the on-board processing takes place as soon as possible after harvesting. It is thus important that this can take place in a facility that is compact and which has such properties that is not severely affected by waves that can make a vessel heel.

SUMMARY

The disclosure provides a system and/ or a reactor for the hydrolysis of raw material which is able to produce consistent reaction conditions for all material that is supplied, regardless of changes in external conditions.

The disclosed reactor provides advantages associated with both batch processes and continuous processes when the contact time between the components included in the process is a critical parameter for product quality.

The disclosed embodiments provide the above benefits by means that are convenient and inexpensive in industrial scale.

Particularly, the disclosure provides a reactor for the hydrolysis of marine raw material on board a vessel with limited space, which is able to provide consistent reaction conditions under varying wind and wave conditions.

The material to be treated in the reactor is partly referred to as "the raw material", partly as "the material".

The disclosed reactor can be manufactured compact in that the reactor externally can have the form of a standing cylinder where the reactor chambers are located with a given inclination relative to the horizontal plane, while the reactor as a whole has a generally vertical orientation. The reactor chambers are tubular and preferably have a circular cross section with the exceptions indicated by the enclosed drawings and the discussions of same. The inclination of each chamber may vary, but is preferably at least 1/10 (vertically/horizontally) [5.7 degrees]. For some embodiments the inclination can be 1/5 [11.3 degrees].

Required heat exchange can be realized concentrically with and within this vertical coil of reactor chambers. Stirring takes place by means of supplied inert gas being bubbled through the reactor chambers. Valves between all reactor chambers ensure uniform residence time in each reactor chamber and therefore uniform total residence time in the reactor. Transportation of partially treated material from one reactor compartment to the next can be performed by supplying an excess of pressure of the inert gas used for stirring while the upstream valve is closed and the downstream valve an open in the reactor chamber in question.

BRIEF DESCRIPTION OF THE DRAWINGS

The invention is below described in further detail with reference to the accompanying drawings, where.

DETAILED DESCRIPTION

Figure 1:
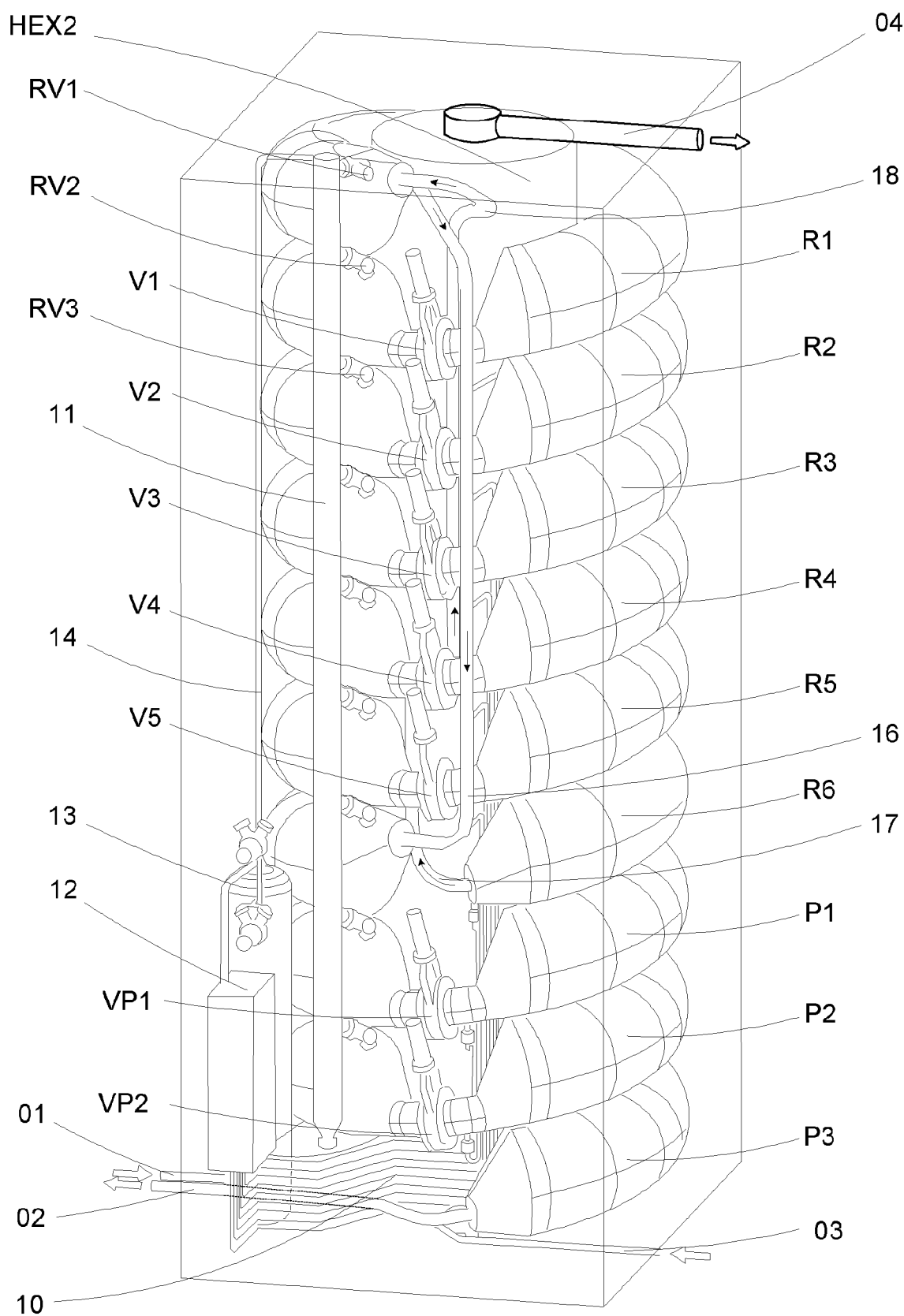
FIG. 1 shows in perspective a first embodiment of the reactor according to the disclosure.

FIG. 1 generally shows an embodiment of a reactor of the disclosure. A number of reactor chambers R1-R6 are coiled up helically downwards into the reactor which as a whole can be said to have a vertical orientation or a vertical axis. An arbitrary reactor chamber can be termed Ri where i is to be viewed as an index. Each reactor chamber R covers circumferentially close to 360 degrees, that is, a full circle. Each reactor chamber Ri is followed by a valve Vi, where i is to be viewed as an index, separating it from the next chamber. Reactor chamber R1 is thus followed by the valve V1. The valves V1-V5 which separates the chambers from each other, is in the shown embodiment aligned over one another. This is for convenience and is not an essential feature of the reactor. Below the reactor chambers there are three pasteurizing chambers P1-P3 in the illustrated embodiment, having substantially the same shape and size as the reactor chambers. These are also separated by valves, numbered as VP1 and VP2. The exact number of reactor chambers and pasteurizing chambers may vary.

FIG. 1 also shows the supply conduit 01 for raw material, discharge conduit 02 for processed material. Also shown are a pressure tank 13 for inert gas, a number of pipes 10 for inert gas to each of the reactor chambers and pasteurizing chambers, a manifold 11 for used inert gas and a return conduit 14 for recycling the used inert gas to the container 13, via a compressor 12. The inert gas is discharged from reactor chambers via valves generally designated RV1 (where i is to be viewed as an index). Three of these are shown with numbers in FIG. 1, RV1-RV3.

FIG. 1 furthermore shows a supply conduit 03 for air to at least one heat exchanger and outlet 04 for air from a heat exchanger, designated HEX2. In practice, two heat exchangers will typically be used as explained later.

FIG. 1 also shows a conduit 17 for the processed material from the reactor chamber R6 to the heat exchanger HEX2. Also shown is a conduit 16 from the upper part of the heat exchanger HEX2 to the inlet of pasteurizing chamber P1. FIG. 1 also shows a portion of a conduit 18 which brings the heat exchanged feedstock into reactor chamber R1.

Figure 2:
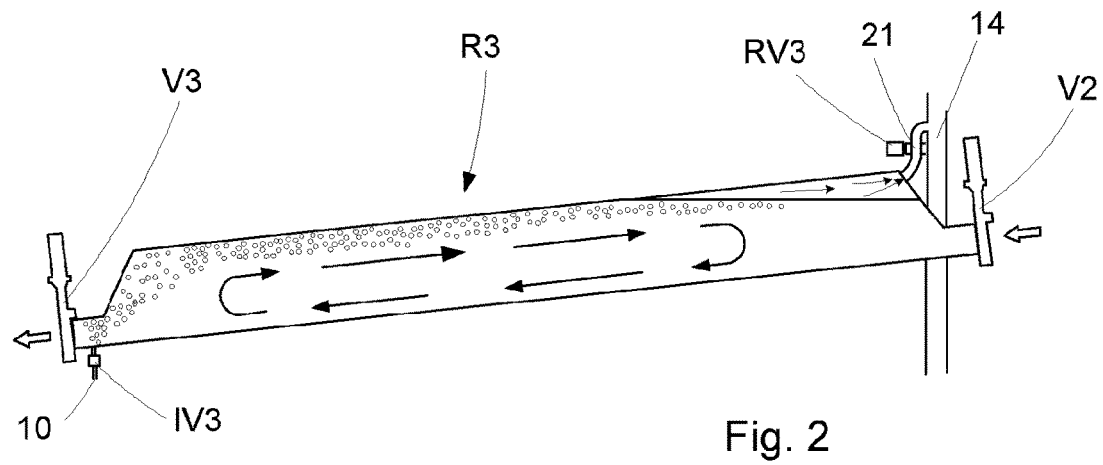
FIG. 2 is a schematic view of one reactor chamber according to an embodiment.

FIG. 2 shows a cross-section of a single reactor chamber, here chamber 3 has randomly been chosen. A difference from the embodiment shown in FIG. 1 is that this reactor chamber for simplicity is shown as a straight chamber. It is also possible to realize the present reactor with straight chambers. The material inlet to the reactor chamber R3 is through the valve V2 to the right in the figure while the outlet is via valve V3 to the left in the figure. Due to the inclination of the reactor chamber, the material flow is assisted by gravity. In FIG. 2, the inclination of the reactor chamber is about 1/10. This is often sufficient in practice, but can in some cases be larger, such as 1/5. Inert gas, typically nitrogen, is introduced via the supply conduit 10 near the downstream end of the reactor chamber and discharged through the discharge stub 21 near the upstream end of the reactor chamber. During treatment both valves V2 and V3 are closed, so that the material for a limited period of time remains stationary in the reactor chamber. As the arrows indicate, the transportation of inert gas through the chamber causes a circulation of the material in the chamber. The inert gas is thus used to efficiently agitate the mass being processed. There is a feed valve IV3 on the supply conduit 10 into the reactor chamber and there is also a return valve RV3 on the discharge stub 21 for gas to the manifold 14.

When reactor chamber 3 is to be emptied, valve RV3 is closed and a selected overpressure is applied to the reactor. It is essential that both valves V2 and V3 are also closed. It is assumed that the adjacent downstream reactor chamber R4 have been previously emptied of material and released from any overpressure. Then valve V3 is opened and a rapid pressure release will take place as gas and material are blown into reactor chamber R4, also assisted by gravity. While the gas will be distributed between the two chambers, virtually all solid and liquid materials will end up in reactor chamber 4 for further processing there.

It is to be understood that reactor chamber R3 has only been chosen as an arbitrary example; essentially the same type of treatment takes place in all reactor chambers, and the main reason for using so many separate chambers is to ensure uniform residence time for the entire mass to be treated, the flow of material from the outside behaving approximately as an ideal plug flow from the inlet of reactor chamber R1 to the outlet from reactor chamber R6. The discharge from the reactor chamber R6 is slightly different because the flow of material does not go directly to a below located chamber, but to a heat exchanger for further heating to thereby interrupt the hydrolysis reaction. The temperature of the pulp after this heat exchange may typically be 90° C. or more.

The skilled artisan will understand that from a situation where all reactor chambers are filled with material for processing, the material in reactor chamber R6 must be emptied before any other chamber, then reactor chamber R5 before reactor chamber R4 etc. However, to make room for the material to be evacuated from reactor chamber R6, it will be necessary to make room by means of a similar procedure for the pasteurizing chambers P1-P3 that is by discharge of the chambers P3, P2 and P1 in this order.

The heat exchange in the reactor is basically classical and can be performed the same way and in the same type of equipment as in prior art processes. It is advantageous, however, both in view of space and other considerations that it is performed in a heat exchanger which is coaxial with the reactor chambers when these are arranged so that they together form a helix.

Figure 3:
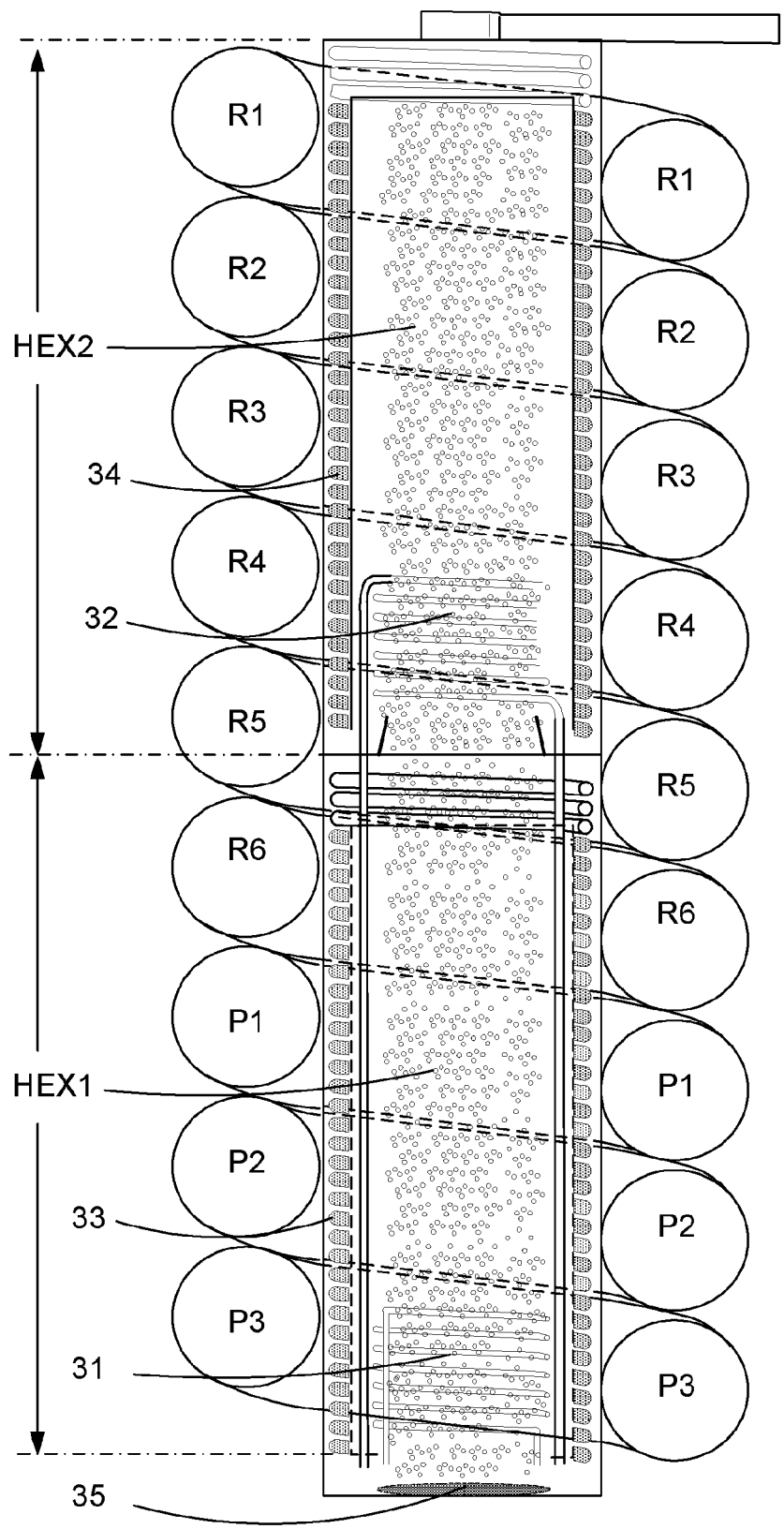
FIG. 3 is a schematic sectional view of certain details of the embodiment of FIG. 1.

FIG. 3 shows a vertical cross-section of a system for heat exchange which may be included as an integral part of the reactor. The reactor chambers R1-R6 are shown in the figure as are also the pasteurizing chambers P1-P3. Coaxially with these and with the vertical axis of the reactor, the superposed two heat exchangers HEX1 and HEX2 are arranged, which may also be perceived as one two-stage heat exchanger. The purpose of the lower heat exchanger HEX1 (or lower stage of the heat exchanger) is to heat the material to a temperature that supports the enzymatic hydrolysis, typically a temperature of about 50° C. This is performed with the flow of material supplied to the reactor through the supply conduit 01 (FIG. 1) before the material enters reactor chamber R1. The material flow supplied to the heat exchanger HEX1 via supply conduit 01 passes, in the illustrated embodiment, upwards through the heat exchanger HEX1 in a helically arranged conduit coil 33 near the outer wall of the heat exchanger. Heat is supplied the heat exchanger to heat exchange device 31. The heat exchanger HEX1 is generally filled with a liquid, preferably an aqueous liquid. In the illustrated embodiment, moreover, air is supplied to the heat exchanger from air supply 03 via a manifold 35. The air helps to circulate water upwards near the centre of the heat exchanger while the water circulates down again along the periphery of the heat exchanger where the helical conduit coil 33 is located, so that the heat exchange in relation to the conduit coil 33 essentially has the character of counter-current heat exchange.

Figure 4:
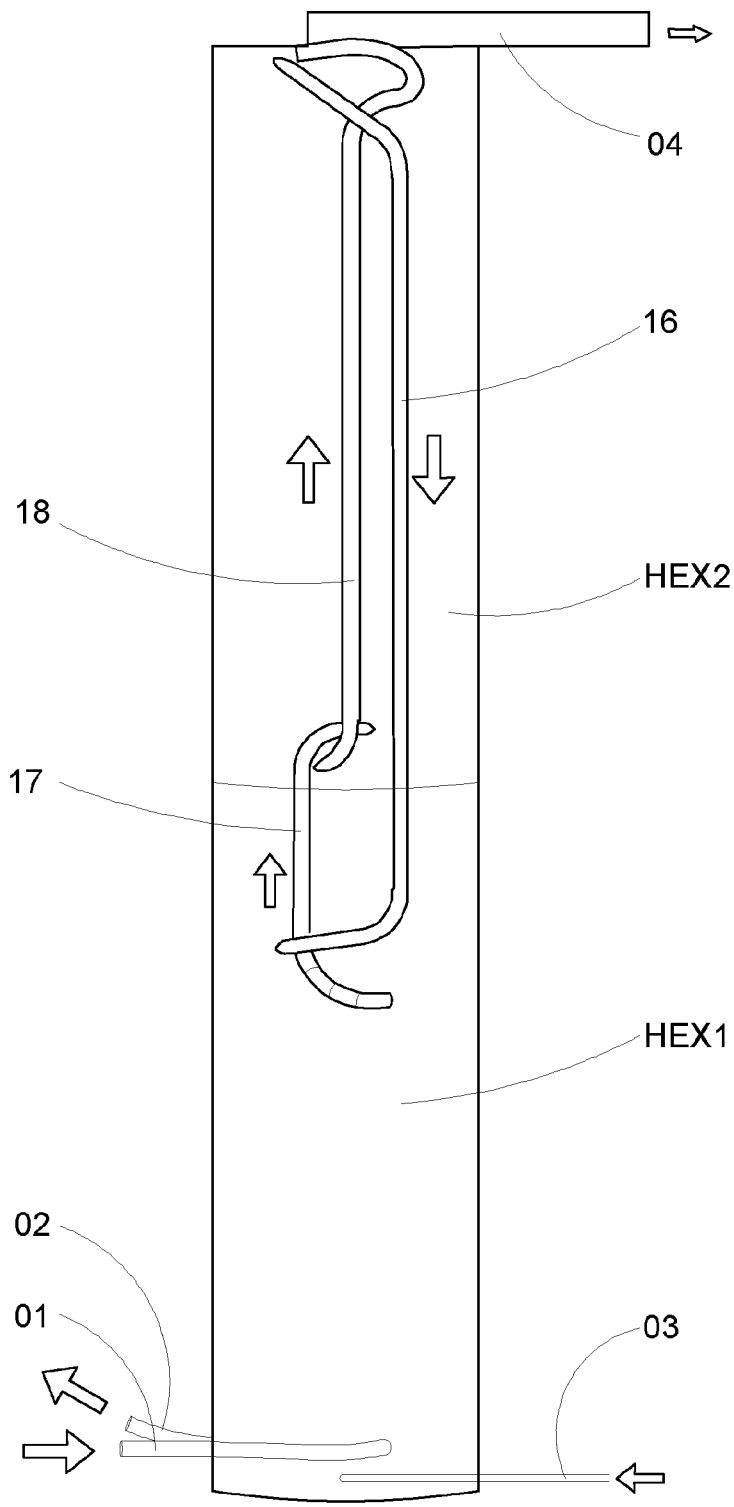
FIG. 4 is a schematic view showing further details of the embodiment of FIG. 1.

We now refer to FIG. 4 as well as to FIG. 3. The outlet of the conduit coil 33 is connected to conduit 18 (FIG. 4) which brings the heated raw material to reactor R1. Typical temperature of the material mixture into R1 is 50° C., but it may vary a few degrees up or down. The actual, measured real time temperature of the material in the reactor R1 or out of the conduit coil 33 may be used to control the gate opening of the heat exchange unit 31.

Heat exchanger (or heat exchange step) HEX2 has the same general construction as heat exchanger HEX1. Material treated in the reactors R1-R6 is supplied to a heat exchanger HEX2 in a helically upward conduit coil 34 which is located near the wall of the heat exchanger, via a conduit 17. A heat exchanger unit 32 supplies necessary heat to the heat exchanger HEX2 so that the material passing through the conduit coil 34 is heated to a temperature high enough to terminate the enzymatic hydrolysis. A suitable temperature can be ca. 90° C. or more. The actual, measured real time temperature of the material out of the conduit coil 34 can be used to control the gate opening on the heat exchanger unit 32. The material leaving the heat exchanger HEX2 is fed to the first pasteurizing chamber P1 via a conduit 16.

FIG. 4 shows parts of the reactor 1 stripped for reactor chambers and pasteurizing chambers, for more clearly to show the outer conduit connections. This being conduit 01 for material supply, conduit 02 for processed material, conduit 03 and 04 for air to and from heat exchanger respectively, conduit 17 for transfer of material from reactor chamber R6 (FIG. 1) to second heat exchanger HEX2, conduit 18 for transfer of material from the first heat exchanger HEX1 to first reactor chamber R1 (FIG. 1), and conduit 16 for transfer of material from second heat exchanger HEX2 to first pasteurizing chamber P1 (FIG. 1).

It should be emphasized that the heat exchangers described herein only represent an example of a suitable layout of the heat exchangers and that any heat exchanger which makes it possible to heat the raw material to a temperature which supports enzymatic hydrolysis and any heat exchanger which makes it possible to heat the treated material to a higher temperature to stop the enzymatic hydrolysis of the material, can be used. It is preferred, however, to use the available volume along the axis of the vertical reactor to the heat exchange, and the shown principle of helical material loop and bubbling of air through the heat exchangers, is convenient because it provides a good temperature distribution in the heat exchangers and in practice a substantially counter-current heat exchange, due to the fact that air pulls the liquid upwards near the vertical axis of the heat exchangers, while the liquid circulated down again near the periphery of the heat exchangers.

Figure 6:
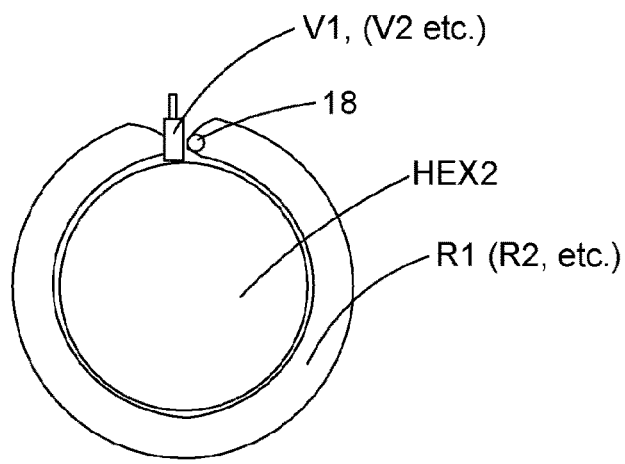
FIG. 6 is a schematic and simplified top view of the reactor shown in FIG. 1.
Figure 5:
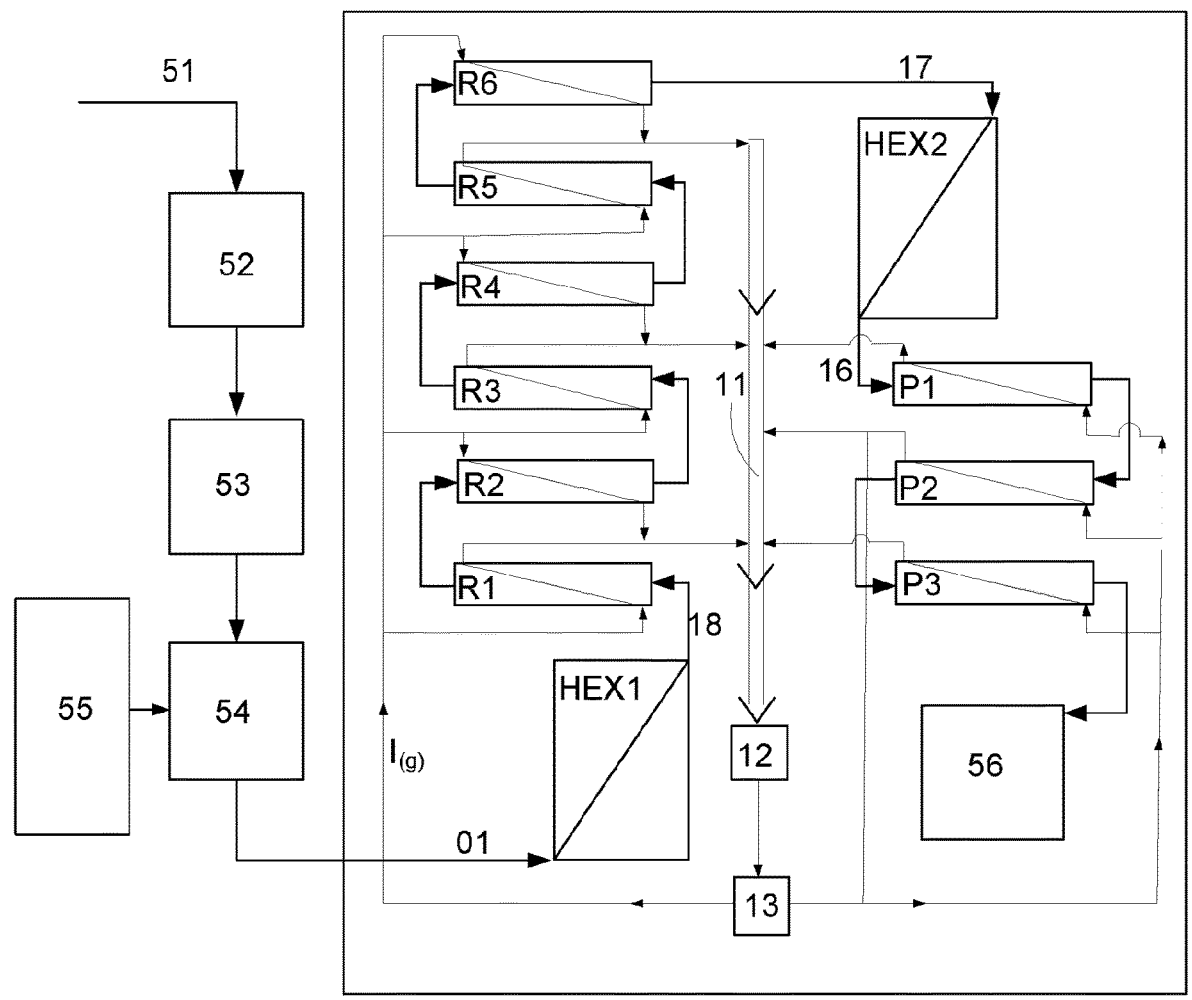
FIG. 5 is a schematic view of a flow sheet over a process utilizing the reactor according to the disclosure.

FIG. 5 schematically shows the process flow for a process utilizing the apparatus as shown in the embodiment of FIGS. 1-5. To the far left a supply of raw material 51 to a feed tank 52 is shown, furthermore a mill 53 for convenient subdivision of the raw material and a pump 54 for feeding the material into the reactor. The pump 54 also sucks in a desired amount of enzyme from enzyme container 55, where the enzyme can be suitably diluted. The components 52 to 55 do not constitute part of the reactor of the present invention and may include any suitable tanks, mills or pumps. In addition to the material flow, FIG. 6 shows also how the inert gas circulates from container 13, via the various reactor chambers and back to container 13 via manifold 11 and compressor 12. A container 56 for the finished treated material is also shown.

FIG. 5 also schematically shows the flow of inert gas (g) from a container 13 through the reactor and back to container 13 via a manifold 11, optionally a not illustrated return conduit 14, and a compressor 12.

FIG. 6 shows schematically and simplified a top view of the reactor shown in FIG. 1, with the reactor chamber R1 coiled around the heat exchanger HEX2, valve V1 (and below this, the valves V2, V3, etc.). Conduit 18 for supplying raw material is indicated, while the flow of inert gas in the system is omitted.

Figure 7:
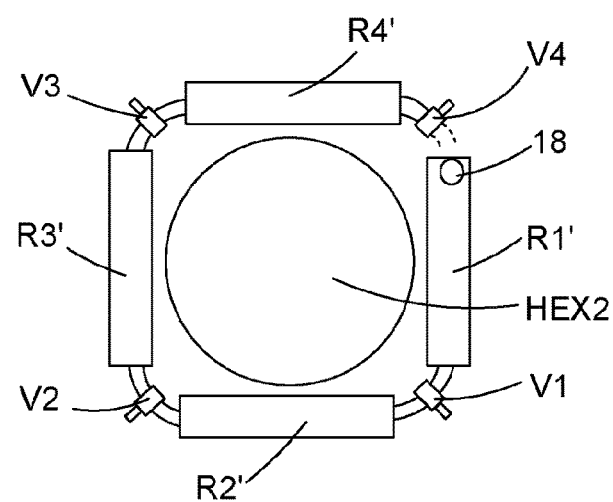
FIG. 7 is a schematic and simplified top view of a reactor according to the disclosure which constitutes a variant to the one shown in FIG. 1.

FIG. 7 shows a view of an alternative embodiment relative to that shown in FIG. 1, where the reactor chambers R1 'to R4' are straight. It is not apparent from FIG. 8 that also in this case the reactor chambers are arranged with inclination. Additional reactor chambers can be provided below the illustrated ones; as an example a reactor chamber R5' below reactor chamber R1', a reactor chamber R6' below reactor chamber R2' etc.

Figure 8:
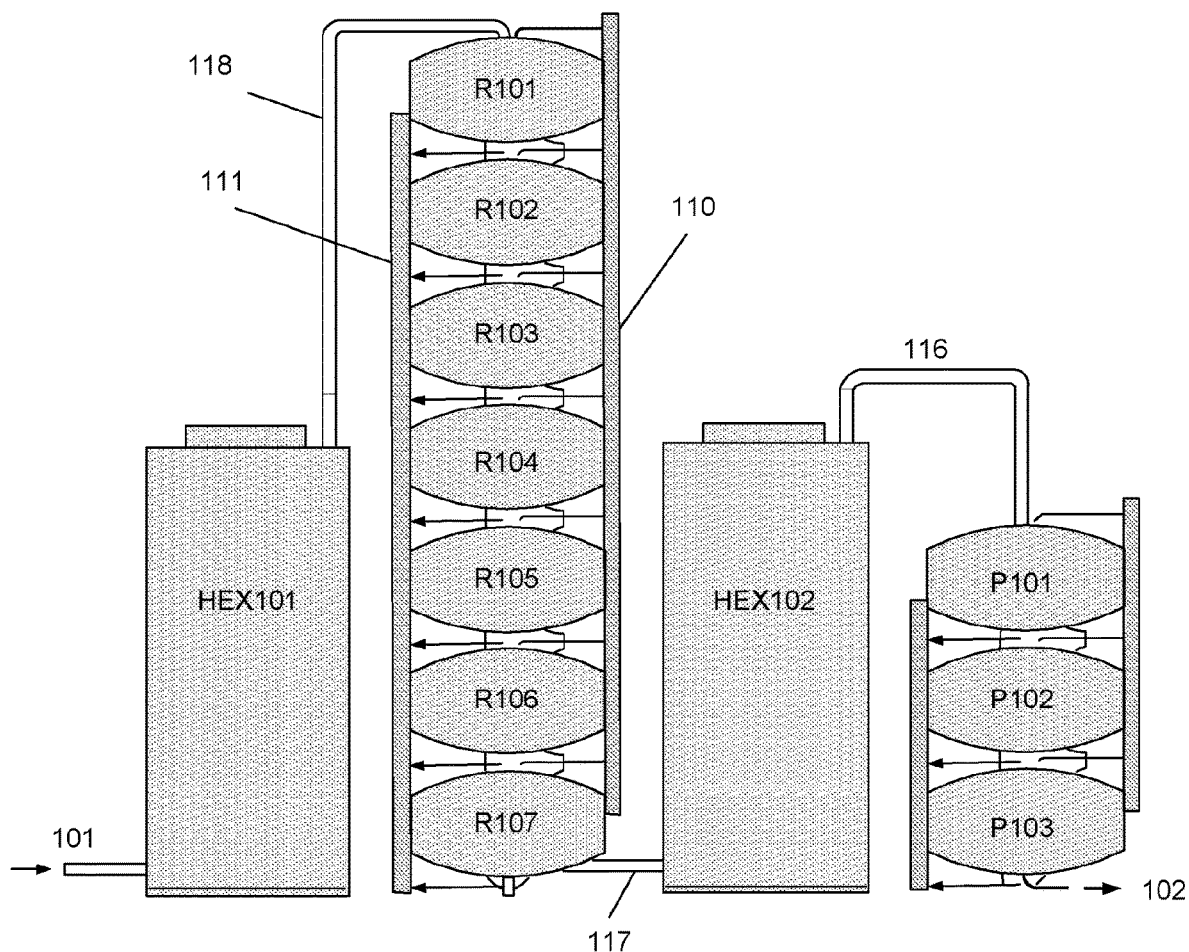
FIG. 8 is a side view of a further embodiment of the reactor according to the disclosure.

FIG. 8 shows an alternative embodiment of that illustrated in the preceding figures.

Details shown in FIG. 8 have numbers in the same series as in FIG. 1, with an addition of 100.

There are two main differences between these embodiments, one consisting in that the reactor chambers R101-R107 and pasteurizing chambers P101-P103 are not tubular, but having the form of more regular tanks, preferably without sharp corners where material undesirably may collect. The other difference is that the reactor system is arranged so that it occupies less space in height and more space in the form of the floor area, specifically that the heat exchangers HEX101 and HEX102 are located beside each other, not superposed, and that the pasteurizing chambers are not positioned below the reactor chambers, but laterally adjacent to the reactor chambers.

The local space conditions are thus an important factor with regard to which embodiment is most favourable; if one has more space in the form of floor area than height, the variant of FIG. 8 being the most preferable one. Moreover, the system as illustrated still comprises a first heat exchanger HEX101 intended to heat supplied material to a temperature which supports enzymatic hydrolysis while heat exchanger HEX102 is arranged to heat the material mixture received to a higher temperature than temperatures supporting enzymatic hydrolysis.

Furthermore there are seven reactor chambers R101-R107 which are all stirred by means of inert gas and wherein the material transportation from reactor chamber R101 to R107, step by step (five steps) takes place to lower vertical levels so that the transfer is supported by gravity. Discharge of the system can also take place in the same manner as described above, using supply of gas at elevated pressure.

The system of FIG. 8 further includes three pasteurizing tanks which can have the same regular shape as reactor chambers R101-R107. In this embodiment, it is less important than in the embodiment shown in FIG. 1 that the pasteurizing chambers have the same shape and the same size as the reactor chambers, but it is still a natural choice that they are substantially equal, specifically because it is easier and more efficient to produce chambers of uniform size and shape.

FIG. 8 shows supply of raw material 101, discharge of processed material 102, conduit 118 for material transportation from the first heat exchanger to the first reactor chamber, conduit 117 from the last reactor chamber to the second heat exchanger, conduit 116 from second heat exchanger to the first pasteurizing chamber, supply conduit 110 for inert gas and manifold 111 for used inert gas to be used again.

It should be emphasized that while FIG. 8 does not show details such as compressor for inert gas, pressure vessel for same, or supply and discharge of heat medium to the heat exchangers, the skilled person would have no difficulty in selecting the proper equipment for such items.

In the following a practical example of using the reactor in a typical usage situation is provided.

A partition wall may separate conduit coils 33 and 34 from the central mass of water in each of the heat exchangers HEX1 and HEX2. Thereby the principle of the heat exchange having the form of counter-current heat exchange is additionally enhanced.

There should be an "aperture" between the coils of the coil pipe, between the conduit coils and the outer wall, and between the conduit coils and the partition wall when such one is present. This is to achieve the best possible heat transfer. With a diameter for example of 60 mm, an aperture of e.g. 20 mm may be used. When using partition wall, this naturally ends at distance from both top and bottom of the heat exchangers to allow the water to turn down at the top and turn up again at the bottom.

Heat supplied to heat exchangers units 31 and 32 may typically be in the form of hot water, steam, or a combination thereof.

The product temperature is determined in practice primarily by the following variables:

a—The rate of the product flow up through the conduit coil. The rate will vary over time in even transitions, controlled by a pump which typically can be a double-acting piston pump.

b—The rate of the hot water counter-currently to the conduit coil can be varied in line with the product flow, by controlling the rate of feed air to manifold 35.

c—The temperature of hot water. Gate opening of steam/hot water for heat exchangers device 31 can be controlled in accordance with temperature of the residual raw material as it leaves the heat exchanger HEX1.

Heat exchanger HEX2 is used to pasteurize the product after hydrolysis to "kill" the enzyme activity and to prevent bacterial growth.

The temperature of the raw material may have fallen approximately 3° C. during the time it takes to hydrolyse the raw material. Thereafter, it is heated in the heat exchanger HEX2 for example to 95° C. The relationship between the height of the lower (HEX1) and upper HEX2) heat exchanger can be adjusted by temperature differences: 5-48° C. and 45-95° C. The air flows out into the open after having set the water in both chambers in motion.

The dimensions of reactor chambers R1-R6 may vary, but a typical size may be 600 mm diameter, that being whether the reactor chambers are helical or straight. The passages between individual chambers, at which the valves are arranged, may be of the order of 150 mm. All valves in the reactor, either for bulk material or inert gas etc., may advantageously be arranged to be automatically controlled. The way of controlling these does not form part of the inventive concept disclosed herein and therefore not described any further here.

The processing time in each chamber can vary and can typically range from 5 to 15 minutes. The number of chambers in the reactor will naturally affect this, as well as the type of raw material used.

The disclosed reactor is suitable for use on board harvesting vessels and do not need to stand vertically to function. An inclination of reactor chambers of 1:10 (vertical/horizontal) is normally enough for use even at sea. If desired to ensure functionality at more severe heel, the inclination can be increased, for example, to 1:5.

Although not being s a central part of the inventive concepts of the disclosure, it is to be noted that the reactor embodiment of FIG. 1, with relevant dimensions of the reactor chamber and heat exchanger, can be embedding in a standard 20 feet container erected vertically; that is with a total height of about 6 meters. The reactor shown in FIG. 8 can do with a substantially lower overall height, but does not allow being embedded in a container.

The principles of the present reactor, however, can also realize whether or not such a height is available. For example, the reactor chambers can be arranged in a column while the pasteurizing chambers can be provided in a separate column disposed alongside, so that the reactor builds less in height and more in width than the one shown in the accompanying drawings.

The invention claimed is:

1. A reactor for enzymatic hydrolysis of a material comprising in sequence:
 a first heat exchanger (HEX1) adapted to heat raw material to be supplied to the reactor to a first temperature within a range favouring enzymatic hydrolysis;
 a reactor comprising a plurality of serially connected reactor chambers (R1-R6) separated by closable airtight valves (V1-V5), the reactor chambers being positioned at different vertical levels relative to one another;
 a second heat exchanger (HEX2) adapted to heat a reaction mixture to a temperature higher than the first temperature,
 wherein a first reactor chamber (R1) is positioned vertically above the other reactor chambers, and a last reactor chamber (R6) is positioned vertically below the other reactor chambers and at least one of the reactor chambers is adapted to be stirred with a through-flowing inert gas introduced via a supply conduit (10), and wherein a return conduit (14) is configured to recycle the inert gas.

2. The reactor of claim 1, wherein each reactor chamber has uniform size and shape and lies symmetric about a vertical axis.

3. The reactor of claim 1, wherein said reactor chambers are tubular and inclined and connected so that the assembly is symmetrical about a vertical axis.

4. The reactor of claim 1, wherein all of the reactor chambers are (R1-R6) adapted to be stirred with through-flowing inert gas being supplied near a downstream end of the respective reactor chambers and discharged near the upstream end of the respective reactor chambers.

5. The reactor of claim 1, wherein the reactor chambers (R1-R6) are curved and assembled relative to one another to form a helix.

6. The reactor of claim 3, wherein at least one of the first heat exchanger (HEX1) and the second heat exchanger (HEX2) is arranged along the vertical axis of the reactor.

7. The reactor of claim 3, wherein the first heat exchanger (HEX1) and a second heat exchanger (HEX2) are arranged above each other along the vertical axis of the reactor.

8. The reactor of claim 5, wherein the first heat exchanger (HEX1) and the second heat exchanger (HEX2) are arranged one above the other, concentrically within the helix.

9. The reactor of claim 1, wherein at least one pasteurizing chamber (P1-P3) is positioned downstream of the second heat exchanger (HEX2).

10. The reactor of claim 9, wherein the at least one pasteurizing chamber (P1-P3) is a tubular chamber of substantially the same shape as reaction chambers (R1-R6).

11. The reactor of claim 3, further comprising an outer housing enclosing the reactor chambers and both heat exchangers.

12. The reactor of claim 1, wherein the inert gas is adapted for recirculation and reuse.

13. The reactor of claim 3, wherein the reactor chambers (R1-R6) have an vertical/horizontal inclination of at least about 1/10.

14. The reactor of claim 1, wherein each reactor chamber (R101- R107) has the shape of a container having a simple, regular shape, and the reactor chambers are arranged vertically above each other with a first reactor chamber (R101) vertically above the other reactor chambers and a last reactor chamber (R107) vertically below the other reactor chambers.

15. The reactor of claim 14, wherein each reactor chamber (R101-R107) has a lowest point at a discharge point for the material in the reactor chamber.

16. The reactor of claim 14, comprising a plurality of pasteurizing chambers (P101- P103), wherein each pasteurizing chamber has the shape of a container with a regular shape and is arranged vertically above one other with a first pasteurizing chamber (P101) being vertically above the other pasteurizing chambers and a last pasteurizing chamber (P103) being vertically below the other pasteurizing chambers.

17. The reactor of claim 14, comprising a plurality of pasteurizing chambers (P101- P103), wherein a first heat exchanger (HEX101) is connected upstream of the first reactor chamber (R101) and wherein a second heat exchanger (HEX102) is connected downstream of the last reactor chamber (R107) and upstream of a first pasteurizing chamber (P101).

18. The reactor of claim 14, comprising a plurality of pasteurizing chambers (P101- P103), wherein the reactor is grouped into four groups which are arranged independently of each other laterally adjacent to each other, the first heat exchanger (HEX101) forming the first group, reactor chambers (R101-R107) forming a second group, the second heat exchanger (HEX102) forming the third group while the pasteurizing chambers (P101-P103) form the fourth group.

19. The reactor of claim 1, wherein each reactor chamber (Ri) is arranged for periodically being discharged via a supply of inert gas at an overpressure to each reactor chamber (Ri) and opening of downstream closable valve (Vi).

20. The reactor of claim 1, wherein said first heat exchanger (HEX1, HEX101) is configured to heat the material mixture to a temperature of about 50° C. and the second heat exchanger (HEX2, HEX102) is configured to heat the material mixture to a temperature of at least about 90° C.

21. The reactor of claim 1, wherein the reactor comprises or is adapted to be connected to a feed device (54) adapted to dispense a certain, adjustable amount of enzyme with a certain amount of raw material for hydrolysis.

22. The reactor of claim 1, wherein the reactor is adapted to be stirred with nitrogen as inert gas.

\* \* \* \* \*